(12) United States Patent
Bricker

(10) Patent No.: US 10,726,101 B2
(45) Date of Patent: Jul. 28, 2020

(54) METHODS, SYSTEMS, APPARATUS AND SOFTWARE FOR USE IN ACCEPTANCE AND COMMITMENT THERAPY

(71) Applicant: Fred Hutchinson Cancer Research Center, Seattle, WA (US)

(72) Inventor: Jonathan Bricker, Seattle, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 525 days.

(21) Appl. No.: 15/117,141

(22) PCT Filed: Feb. 9, 2015

(86) PCT No.: PCT/US2015/015066
§ 371 (c)(1),
(2) Date: Aug. 5, 2016

(87) PCT Pub. No.: WO2015/120410
PCT Pub. Date: Aug. 13, 2015

(65) Prior Publication Data
US 2016/0371464 A1 Dec. 22, 2016

Related U.S. Application Data

(60) Provisional application No. 61/937,424, filed on Feb. 7, 2014, provisional application No. 61/969,071, filed on Mar. 21, 2014.

(51) Int. Cl.
*G06F 19/00* (2018.01)
*G16H 10/60* (2018.01)
(Continued)

(52) U.S. Cl.
CPC .......... *G06F 19/3481* (2013.01); *A24F 47/00* (2013.01); *G06F 19/00* (2013.01); *G16H 10/60* (2018.01); *H04L 67/22* (2013.01)

(58) Field of Classification Search
None
See application file for complete search history.

(56) References Cited

U.S. PATENT DOCUMENTS 3,596,463 A * 8/1971 Rudolph .............. G04B 19/283
368/266
4,615,481 A 10/1986 Tanaami
(Continued)

FOREIGN PATENT DOCUMENTS

WO 2013/121200 8/2013

OTHER PUBLICATIONS

NCIcancertopics: "quit Smoking with the NCI QuitPal Mobile App", Dec. 20, 2012 (Dec. 20, 2012), XP054975953, Retrieved from the Internet: URL:https://www.youtube.com/watch?v=079nmEYtXHI.
(Continued)

Primary Examiner — Michael Tomaszewski
Assistant Examiner — Jay M. Patel
(74) Attorney, Agent, or Firm — DWC Law Firm, P.S.

(57) ABSTRACT

Various embodiments of the present disclosure comprise methods, apparatus, systems and software for use in implementing acceptance and commitment therapy (ACT). The methods include notifying or reminding users to track completion of exercises, and to track and/or monitor awareness of urges and the number of times the user allows urges to pass. Also, physical sensors can be employed to help monitor the user's detrimental behaviors and to send notifications or reminders to the user to perform exercises or track urges.

20 Claims, 18 Drawing Sheets

(51) Int. Cl.
*H01L 29/08* (2006.01)
*A24F 47/00* (2020.01)
*H04L 29/08* (2006.01)

(56) References Cited

U.S. PATENT DOCUMENTS

| | | | | |
|---|---|---|---|---|
| 8,926,320 B2* | 1/2015 | Al Gharib | | A24F 47/00 131/270 |
| 2004/0031498 A1* | 2/2004 | Brue | | A24F 15/005 131/270 |
| 2005/0141346 A1* | 6/2005 | Rawls | | G09B 19/00 368/10 |
| 2007/0061166 A1* | 3/2007 | Ramasubramanian | | G06F 19/328 705/2 |
| 2007/0168501 A1* | 7/2007 | Cobb | | G06Q 30/02 709/224 |
| 2008/0201174 A1* | 8/2008 | Ramasubramanian | | G06F 19/3456 705/3 |
| 2010/0145726 A1* | 6/2010 | Duke | | G16H 50/20 705/3 |
| 2010/0211407 A1* | 8/2010 | Duke | | G06F 19/3481 705/3 |
| 2011/0247638 A1* | 10/2011 | Ayala | | A24F 47/00 131/270 |
| 2011/0263947 A1* | 10/2011 | Utley | | A61B 5/4845 600/300 |
| 2011/0276451 A1* | 11/2011 | Busse | | G06Q 40/00 705/35 |
| 2012/0214107 A1* | 8/2012 | Al Gharib | | F23Q 2/325 431/13 |
| 2013/0216989 A1* | 8/2013 | Cuthbert | | A61B 5/721 434/238 |
| 2014/0142965 A1* | 5/2014 | Houston | | G06F 19/3418 705/2 |
| 2014/0157171 A1* | 6/2014 | Brust | | G06F 3/0481 715/771 |
| 2015/0193597 A1* | 7/2015 | Cederlund | | A61K 31/135 705/2 |

OTHER PUBLICATIONS

Quit Pro—Smoking Cessation App—App Page: "Quit Pro—Smoking Cessation App "Save a life. Help a smoker quit." ", Facebook, Dec. 27, 2012 (Dec. 27, 2012).

* cited by examiner

My Quit Plan

How I will get to quit date: ⟵ 44

42 ⟶ ● Gradually cut back by [ X ] per week

○ Quit "cold turkey" on your quit date

[ Previous ]    [ Next ]

*FIG. 4*

My Quit Plan

50

How to cut back

Give up the easiest cigarettes of the day
Find the ones throughout the day you don't really want.

Only smoke during certain hours

Don't smoke in certain situations
For example, driving, working, or time with your family

[ Previous ]    [ Next ]

70

My Quit Plan

Using Quit Aids

Select which med(s) you would like to use

- [x] Patch ●
- [x] Gum ●
- [ ] Chantix ●
- [ ] Zyban ●
- [ ] Other
- [ ] None

[Previous]  [Next]

*FIG. 7*

My Quit Plan

Inner Circle:

Who supports you? Think of at least two people.

80  First Name    Email
    [ Name ]      [ Email ]   — 82

[ Previous ]    [ Next ]

*FIG. 8*

Plan completed: Feb 5, 2014

What inspires me to quit:
Family
Leisure
Other

My quit date is:
Mar 10, 2014

I will quit by:
eliminating 1 cigarette(s) per day

How I'll cut back:
give up the easiest one of the day
only smoke during certain hours

About my smoking:
I smoke about 20 cigarettes/day, costing me $230 each month.

I plan to use these medications:
the patch

My supportive Inner Circle:
d
yyyyyy@------.com

*FIG. 10*

METHODS, SYSTEMS, APPARATUS AND SOFTWARE FOR USE IN ACCEPTANCE AND COMMITMENT THERAPY

CROSS REFERENCE TO RELATED APPLICATION(S)

This application is the US national phase entry of International Patent Application No. PCT/US2015/15066, filed Feb. 9, 2015, which claims priority to U.S. Provisional Patent Application No. 61/969,071, filed Mar. 21, 2014, and U.S. Provisional Patent Application No. 61/937,424, filed Feb. 7, 2014, both of which are incorporated by reference herein in their entireties.

BACKGROUND

1. Technical Field

The present disclosure relates to methods, systems, apparatus and software for use in acceptance and commitment therapy, and in particular, to habit modification.

2. Related Art

On the fiftieth anniversary of the landmark 1964 Surgeon General's Report on Smoking and Health, the 2014 Surgeon General report concludes that tobacco use remains a leading public health challenge of our time. Cigarette smoking: (1) accounts for 480,000 deaths; (2) remains the number one preventable cause of premature death; (3) causes diabetes and multiple cancers including colorectal and liver cancers; and (4) leads to $289 billion in healthcare and lost productivity costs annually in the US alone. The decline in smoking prevalence has slowed in recent years, resulting in approximately 42 million Americans still smoking. As states' funding for population-level smoking cessation programs (e.g., quitlines) remain far below their CDC-recommended levels, there is a tremendous need for intervention technologies with great potential population-level impact at the lowest possible cost.

Population-level impact is driven by reach and effectiveness. Regarding reach, there are already 400 smoking cessation mobile device software applications (or "apps"). The top 50 Android-based smoking cessation apps alone were downloaded to smartphones an average of approximately 780,000 times per month in early 2012—As a point of reference, smoking cessation quitlines, available in all 50 states, together serve an average of about 42,000 smokers per month. The reach of quit smoking apps will continue to grow. As of the beginning of 2014, the majority (approximately 56%) of all US adults owned smartphones, including about 64% of African Americans and about 64% of Hispanics. Approximately eighty percent of all new cellphone purchases are smartphones, and the greatest growth rate is among those with low income. US adult smartphone ownership is projected to reach at least 90% by 2020. Based on these trends, quit smoking smartphone apps have strong reach that will rapidly increase as smartphone ownership continues to climb. Indeed, smartphones ownership is strong among low income and racial/ethnic minority populations. These two subgroups, who have low smoking cessation rates, have not been well reached by smoking cessation websites, probably primarily due to their low rates of personal computer ownership.

Regarding effectiveness, the currently recommended intervention content commonly believed to be most effective are the US Clinical Practice Guidelines on offering quit planning, skills training, advice on pharmacotherapy, and interactive social support for quitting. Indeed, two recent reviews scored the 100 most popular smoking cessation apps for their level of adherence to the US Clinical Practice Guidelines. They concluded that the key to an apps' effectiveness is closely following these guidelines. However, unfortunately, even websites and text messaging interventions that follow these guidelines are not very effective. Multiple recent meta-analyses of websites and text messaging interventions report that their average 30-day point prevalence quit rates at 12 months post-randomization are remarkably similar, ranging from 7% to as high as 10%, for those that closely follow the US Clinical Practice Guidelines. Regarding the effectiveness of quit smoking apps, as of Feb. 7, 2014, only one randomized trial had been published. While it had severe limitations (e.g., N=101; 3 month follow-up) and is only the first trial, results merely extend a well-established pattern found in the website and text messaging quit smoking literature. Specifically, this study reported that an app which closely followed US Clinical Practice Guidelines was no more effective than text messaging. Thus, apps that follow the US Clinical Practice Guidelines, and research in testing apps that just follow these guidelines, are both destined to make only modest scientific and population-level impacts, if any.

One form of clinical behavior analysis that has shown effectiveness for addressing detrimental addictions and conditions involving behavior is Acceptance & Commitment Therapy (ACT). ACT focuses on increasing willingness to experience physical cravings, emotions, and thoughts while making values-guided committed behavior changes. In ACT, acceptance includes making room for intense physical cravings (e.g., urges to smoke), emotions (e.g., sadness that triggers smoking), and thoughts (e.g., thoughts that trigger smoking) while allowing them to come and go. Commitment in ACT includes articulating what is deeply important and meaningful to individuals—i.e., their values—to motivate and guide specific plans of action (e.g., stopping smoking). Despite ACT's apparent effectiveness, the application of ACT through an app raises numerous challenges.

BRIEF SUMMARY

In some embodiments, methods of assisting in behavior adjustment, such as, for example, smoking cessation, or refraining from other unwanted behavior, are provided. The methods can include, among other things, receiving a target date for a user to adjust a behavior and/or photographs to help remind the user of motivations. In the case of refraining from an unwanted behavior, the method can comprise displaying one or more screen modes displaying a first indicia in association with an invitation to the user to track acceptance of an urge (e.g., urges for the unwanted behavior) without regard to whether the user acts on the urge, and receiving an input from the user in response to the user actuating (e.g., tapping or touching) the first indicia for indicating that the user has tracked an acceptance of the urge regardless of whether the user acts on the urge. The method can also comprise displaying progress information to a user in relation to the behavior adjustment, including displaying a number of times the user has tracked acceptance (e.g., awareness) of the urge, regardless of whether the user acted on the urge. It has been found, among other things, that tracking the practice of acceptance skills, regardless of whether the urge is acted on, can significantly increase the odds of adjusting away from the unwanted behavior successfully.

In addition, the method can comprise displaying one or more screen modes displaying a second indicia in association with an invitation to the user to track a number of times the user has refrained from the unwanted behavior by allowing urges to pass. The method can then involve receiving input from the user in response to the user actuating the second indicia for indicating that the user has tracked refraining from the unwanted behavior, and displaying progress information to a user in relation to the behavior adjustment, including a number of times the user has refrained from the unwanted behavior.

In some embodiments, the method also includes displaying one or more auto-triggered reminders, reminding the user to track, a) a number of exercises the user has completed related to acceptance of urges or b) a number of times the user has allowed the urge to pass or c) the number of times the user has accepted the urge.

The method can further comprise receiving a user selection to engage in an exercise, and in response to the selection, conveying through audio, text, pictures or video, one or more testimonials from individuals that previously engaged in unwanted behavior that is the subject of the user's behavior adjustment.

The method can also involve receiving a user selection to engage in an exercise, and in response to the selection, conveying through audio, text, pictures or video, reasons why the user is adjusting behavior as a function of information the user previously provided in response to queries in a screen mode; receiving a user selection to engage in an exercise, and in response to the selection, conveying through audio, text, pictures or video, methods or techniques for accepting urges or allowing urges to pass; and receiving a selection from the user to track the user's engagement in one or more exercises, and displaying indicia to the user indicating a number of times the user has engaged in the one or more exercises.

In some embodiments, a calendar can be displayed showing the number of urges the user has tracked in association with corresponding dates on which the urges were tracked, and/or graphically represented badges can be displayed with each of the badges being indicative of one or more tracked activities having been completed.

In some embodiments, a smart device is specially configured for carrying out one or more of the steps recited above, and/or can be specialized hardware, having hardware buttons, such as, for example, keys, that are hard coded and/or labeled accordingly for use in actuating any of the input recited herein in place of the graphical indicia recited.

In some embodiments, a non-transitory computer-readable media has instructions for instructing a smart device for carrying out any of the steps recited above, or elsewhere herein.

In some embodiments, a method for assisting in human behavioral adjustment using a portable smart device is provided, the method comprising displaying at least a first selectable indicia in association with the presentation of audio or visual information inviting a user to track when the user is aware of an urge; receiving data from the user provided by selection of the first selectable indicia, the data indicative of the user having experienced the urge; displaying at least a second selectable in association with the presentation of audio or visual information inviting a user to track when the user has allowed the urge to pass without acting on the unwanted behavior; receiving data from the user provided by selection of the second selectable indicia, the data being indicative of the user having refrained from the unwanted behavior by letting one or more urges pass; displaying a progress screen or calendar screen showing data as a function of the a number of times the user has selected the first selectable indicia and the second selectable indicia within specific time periods; and displaying automated notifications to remind the user to select either the first selectable indicia or second selectable indicia.

In some embodiments, the method can further comprising displaying a current financial cost of smoking for the user; tracking a number of exercises a user has completed related to acceptance of urges, and displaying a graphical badge as a result of completion of a predetermined number of exercises; and/or automatically notifying the user if a frequency with which the user has engaged in an activity (such as tracking an urge or engaging in an exercise) falls below a threshold amount within a particular period of time. In some embodiments, the notification can comprise a message notifying the user of particular statistical data related to smoking quit rates and their relationship to the tracking or completion of exercises or urges.

In some embodiments, the smart device includes a location tracking system and the method further comprises displaying a map showing locations in which the user has engaged in the unwanted behavior over a period of time, according to a tracking function.

In some embodiments, the method can comprise automatically notifying the user to practice an exercise when a location tracking system detects that the user is near a location in which the user has indicated engagement in an unwanted behavior, one or more times over a particular time interval; and/or automatically notifying the user to practice an exercise when the location tracking system detects that the user is near a location in which the user has indicated engagement in unwanted behavior a threshold number of times over a particular time interval.

In some embodiments, the smart device is connected to a carbon monoxide sensor and the method further comprising detecting when the user is smoking using the carbon monoxide sensor and notifying the user to practice an exercise; and/or detecting when the user is smoking and recording a location of the user, and using the recorded location information to automatically remind to the user to engage in exercise when the user is near the locations recorded; and/or detecting when the user is smoking and recording voices proximate the user.

In some embodiments of the present disclosure, a computer implemented method of assisting in behavior adjustment comprises displaying one or more screen modes for use in recording information describing a user's current habits and motivations for behavior adjustment, wherein the information describing the motivations includes personal photographs of the user; displaying one or more screen modes for use in tracking or monitoring urges; displaying a plan of the user that describes the user's tactics for behavior adjustment; and reminding the user to track urges.

BRIEF DESCRIPTION OF DRAWINGS

FIG. 4 is an example screen mode for a graphical user interface for use in designating a quit method in some embodiments of the present disclosure.

FIG. 7 is an example screen mode for a graphical user interface for use in designating medications as quit aids in some embodiments of the present disclosure.

FIG. 8 is an example screen mode for a graphical user for use in designating a support group or individual in some embodiments of the present disclosure.

FIG. 10 is an example screen mode for a graphical user interface showing a quit plan summary in some embodiments of the present disclosure.

DETAILED DESCRIPTION

In the present disclosure, certain specific details are set forth in order to provide a thorough understanding of various embodiments of the disclosure. However, upon reviewing this disclosure one skilled in the art will understand that the various embodiments disclosed herein may be practiced without many of these details. In other instances, some well-known hardware structures (e.g., smart phones, tablets, computers and networking infrastructure), software, internet and cloud-based resources, and wired and wireless network protocol have not been described in detail to avoid unnecessarily obscuring the descriptions of the embodiments of the disclosure.

In the present description, inasmuch as the terms "about" and "consisting essentially of" are used, they mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include" and "comprise" are used synonymously, both of which are intended to be construed in a non-limiting sense, as are variants thereof, unless otherwise expressly stated.

Various embodiments of the present disclosure are described in the context of use by individual tobacco smokers to assist in smoking cessation. However, as will be appreciated by those skilled in the art after reviewing this disclosure, all or some of the methods, systems, software and devices disclosed herein may also have applicability in other context wherein it is desired to assist individuals in managing and/or ceasing or controlling detrimental habits associated with addictions or conditions, either as a supplement to other therapies, or as a primary tool. Such detrimental habits can be, for example, habits prevalent in the context of smokeless tobacco use, weight loss, exercise, diet, alcohol and other drug use, medication adherence, diabetes self-management, gambling, depression, anxiety, and stress.

The descriptions of examples of the present disclosure provided herein are not intended to be restrictive unless otherwise indicated.

Figure 1:
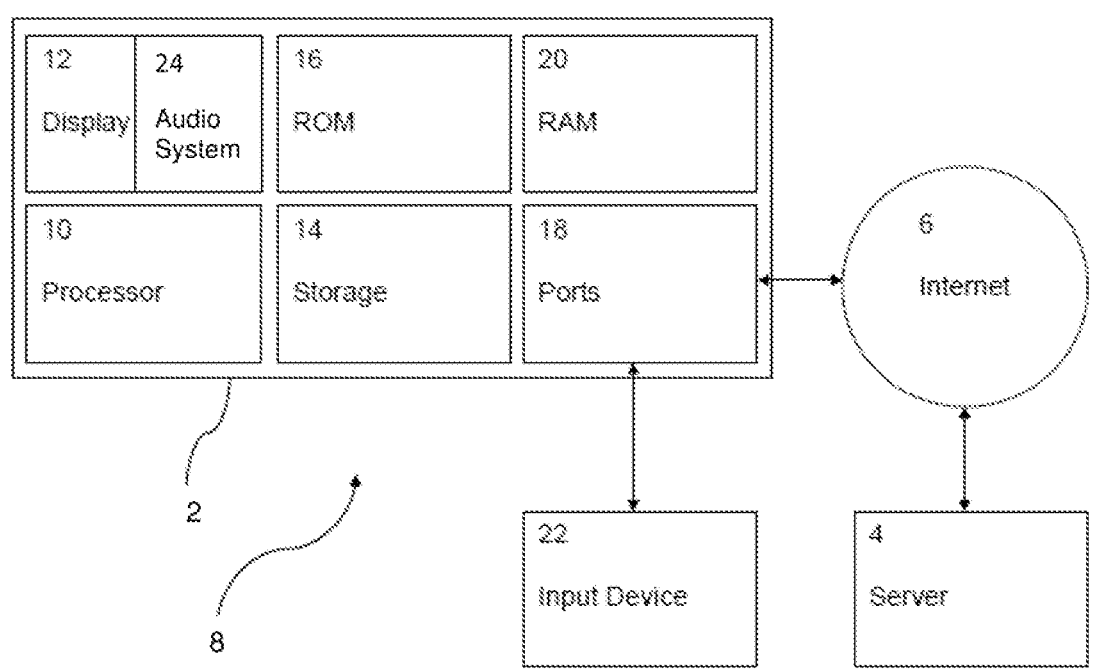
FIG. 1 is a simplified diagram of a smart device and system for use with some embodiments of the present disclosure.

Referring to FIG. 1, in some embodiments of the present disclosure, software application(s) of the present invention may be stored on a user smart device 2, such as a smart phone, or other wireless device (e.g., cell phone, tablet), or wired device, or computer, to execute various tasks associated with the embodiments of the present disclosure. The electronic tasks may be executed either entirely on the smart device 2, or in conjunction with one or more applications residing on a server 4, or host 4, as will be appreciated by those skilled in the art after reviewing this disclosure. A host 4, usable for processing instructions and delivering signals to, and receiving signal from, user devices, may comprise one or multiple servers, to provide aggregate processing capacity and storage capacity, and the host 2 may also be a cloud-based hosting system.

Each user smart device 2 can include a processor 10, display system 12, audio system 24 with speaker(s), non-volatile storage device 14, ROM 16, a plurality of communications ports 18 and communications interfaces, and RAM 20. The plurality of communication ports 18 on smart device 2 can receive control signals from input devices 22 (e.g., touchscreen, keyboard or touch pad and/or mouse), which may be physically integrated into the smart device 2 (such as in the case of a typical smart phone), or may be peripheral, or both. Various communications interfaces can also be provided to enable communications over the network 6 (e.g., Internet), such as wireless communication interfaces or wired communications interfaces.

Figure 18:
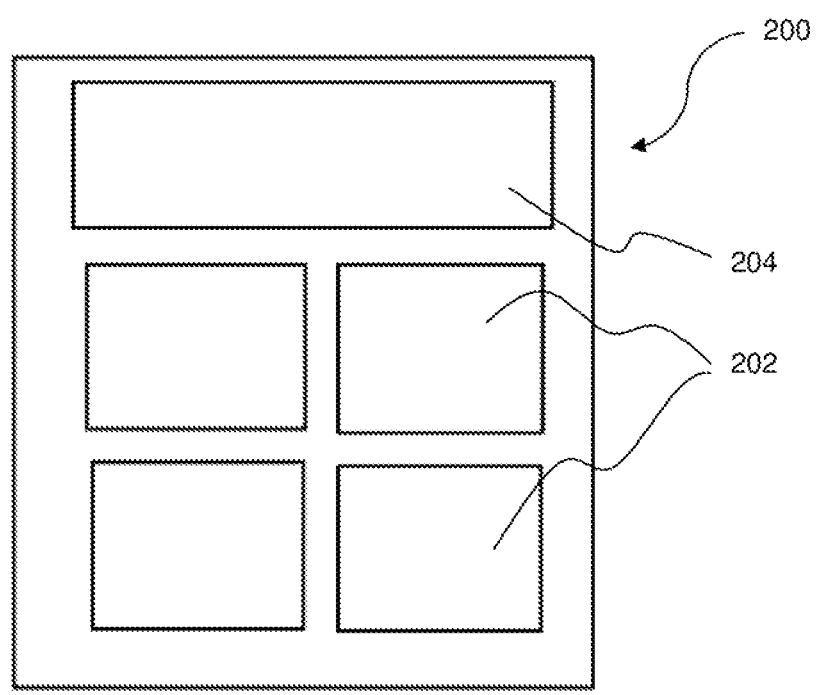
FIG. 18 is a simplified diagram showing an example specialized portable hardware device for use in implementing some embodiments of the present disclosure.

Various embodiments of the present disclosure are described in the context of a smart phone executing a specialized software application ("app"); however, all or many of the features described for the various embodiments may be implemented using specialized software on other smart devices, such as, for example, a desktop computer, laptop, tablet computer, or any other smart device, or firmware on any smart device capable of processing data/information, such as, for example, specialized portable (or stationary) behavior-adjustment hardware carried or worn by a user, having capabilities to receive and process input data/information to generate an output. For example, referring to FIG. 18, specialized behavior-adjustment hardware 200 (as opposed to smart devices having multi-purpose touch screen hardware, such as, smart phones, as also contemplated herein) configured for implementing various embodiments of the method steps described in this disclosure, can be provided with hardware push-buttons 202 or other hardware actuators, etc., in lieu of, or in addition to, the various references herein to graphical indicia usable for actuating input. The specialized behavior adjustment hardware 200 can also be provided with a display 204, and processor, for carrying out the steps recited herein. That is, for example, each of the graphical touch screen indicia described throughout this disclosure usable for providing input for tracking urge awareness, passing urges, or behavioral events or restraint from behavior, or any other event, could be substituted with a hardware push-button 202, or other hardware actuator, which can be labeled for use, as will be immediately appreciated by those skilled in the art after reviewing this disclosure. Also, various embodiments of the present disclosure may be implemented by user access to a website, rather than through an app on a smart device, or may be implemented as a combination of an app plus access to a remote website and/or host, as will be immediately appreciated by those skilled in the art after reviewing this disclosure.

Various embodiments of the present disclosure involve an app combining ACT's intervention content in an innovative manner with the processes, displays, systems and other features described herein.

In some embodiments of the present disclosure, a user can download an app of the present disclosure on the user's smart device 2. The app may be accessible for download through a wireless Internet connection, and the smart device 2 may be a smart phone. The app can be stored on a memory 14 of the smart device, and a processor 10 can execute the app and present a graphical user interface on the display 12 driven by instructions in the app. The graphical user interface can have a plurality of modes, as described further below.

In some embodiment of the present disclosure, upon originally initiating the app, the user can be presented with an introduction video describing the app in metaphorical terms. For example, a one minute digital video (or "video") can be presented on the display 12, with accompany audio on a speakers 24 of the smart device 2, asking the user to think of the program as a car journey, wherein the user is the driver, and in the backseat are passengers who represent cravings to smoke. The driver is carrying the passengers while he navigates his way through the journey of caring for his body. The front passenger represents the app providing navigation through the process of quitting.

After presenting the introduction video, the graphical user interface can display various screen modes for displaying and receiving data, files, and/or information to be entered by the user. For example, the graphical user interface can present various screen modes for setting up a quit plan. The screen modes for setting up a quit plan can include a personal values screen mode, quit date screen mode, quit method screen mode, tactics screen mode, smoker's profile screen mode, medication screen mode, and support group setup screen mode, each of which are described below.

Figure 2:
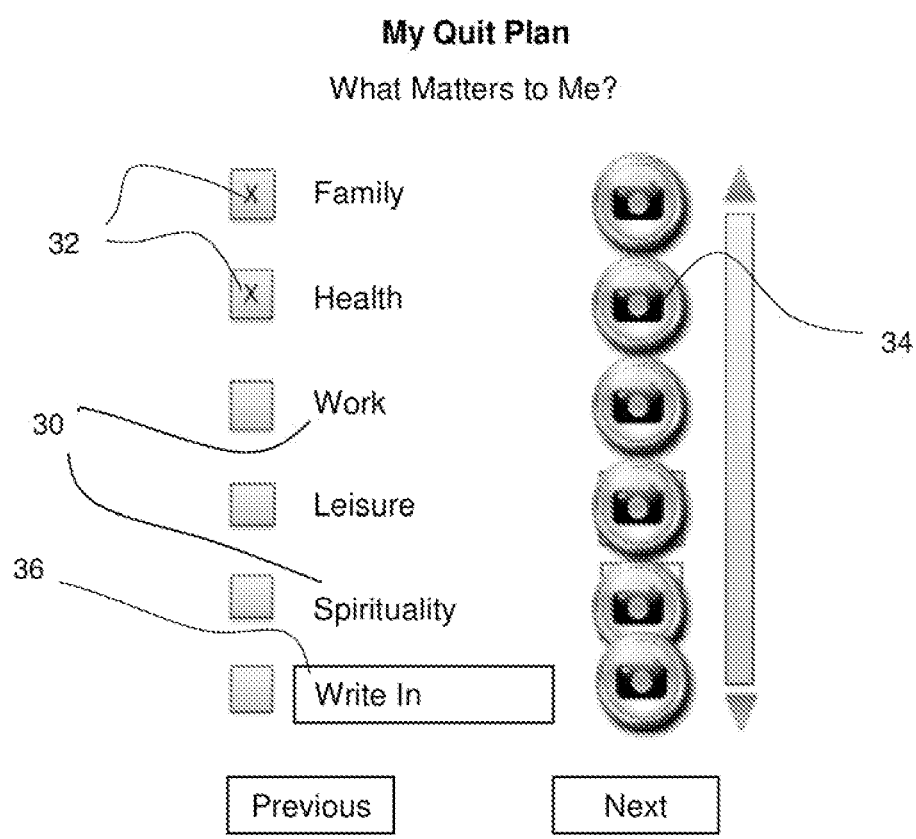
FIG. 2 is an example screen mode for a graphical user interface for use in selecting life domains that define motivating values for a user in some embodiments of the present disclosure.

As part of the quit plan setup, the app can present a personal values screen mode, as shown in FIG. 2, in which the user can select to associate particular photos stored on the user smart device 2 with the app. The photos can represent life domains of high importance to the user. For example, referring to FIG. 2, various life domains can be labeled by different indicia 30, representing different domains in the life of the user. The indicia 30 can be text designating the different domains, such as, for example, "family," "health," "work," "leisure," "spirituality," etc., representing, for example, loving one's family, caring for one's body, ambition for one's career, passion for one's hobbies, and faith in God. For each life domain designated by the indicia 30, a corresponding selection indicia 32 is provided, which can be a graphical selection box 32 the user can select (e.g., by touch screen), if the user wishes to designate the corresponding life domain as important to the user (such designation will later allow the selected life domain to be presented to the user as motivational material when the user is seeking motivation, as will be described further below). If a user selects a graphical selection box 32 corresponding to a life domain 30, the user can also designate a photo (or alternatively in some embodiments, one or more photos), to be associated with the particular selected life domain 30, by selecting a corresponding photo designation indicia 34. If the user selects a photo designation indicia 34, the app can cause a file selection browser to be displayed for use in selecting a digital photograph from the user's library of photos (e.g., photos stored in a memory 14 on the user's smart device 2), to associate the selected photo with the corresponding life domain 30.

Alternatively, in some embodiments, a user can select to a user-writable life domain field 30', in which a user can write in a life domain of the user's selection. The user-written life domain 30' can also correspond to a graphical selection box 32. If the user selects the selection box 32 corresponding to the user-written life domain 30', then during use of the app, that user-written life domain 30' can be presented to the user in association with the user's selection to view motivational materials, as will be discussed further below. Also, after a user configures a user-written life domain field 30', the app can automatically generate another user-written life domain field 30', which the user can select in order to write in another life domain, and so on, and so forth, until the user has written as many user-written life domains as the user desires.

Figure 3:
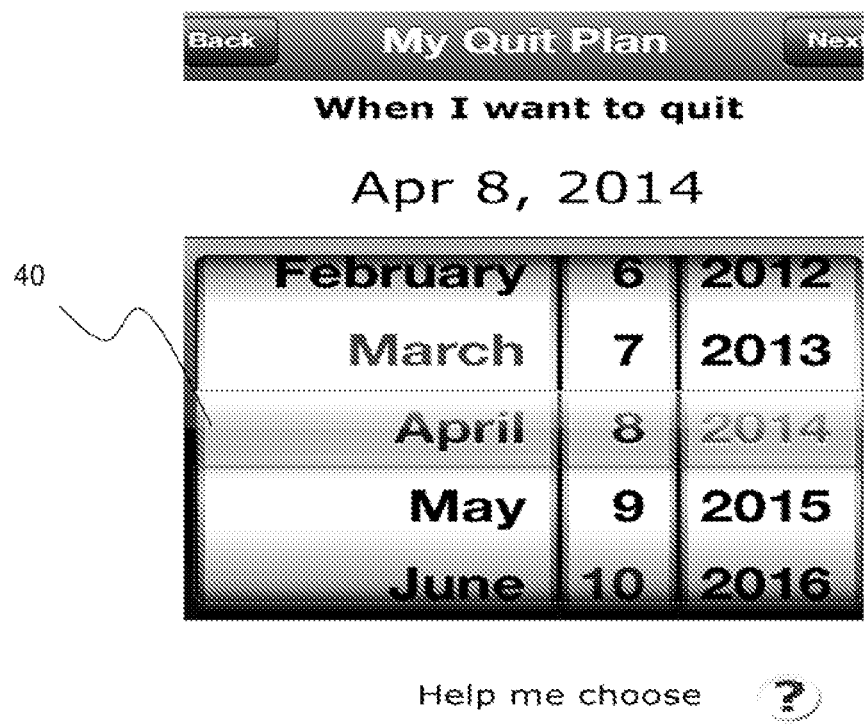
FIG. 3 is an example screen mode for a graphical user interface for use in selecting a target quit date in some embodiments of the present disclosure.

In some embodiments, text can be presented on the described personal values screen mode in FIG. 2 that encourages the user can to select personal photographs (e.g., photographs taken by the user, or taken of people, places or things in the user's life), in order to increase the user's motivation to change detrimental habits Referring to FIG. 3, in some embodiments, a quit date screen mode is presented. This screen mode can include, for example, a scrollable calendar 40 for selecting a targeted quit date for the user, or the date on which the user plans to have the user's last cigarette (i.e., the quit date). Once selected, the quit date is saved by the app and can be displayed to the user anytime the user selects to see a quit plan overview screen mode (described below). In some embodiments, the app can push reminders to the user as the quit date draws near.

In a quit method screen mode, as shown in FIG. 4, the user can select one of two methods for reducing cigarettes smoked leading up until the quit date, by selecting one of two graphical selection indicia 42, one associated with quitting "cold turkey," and one associated with quitting gradually. If, the user selects the selection indicia 42 associated with quitting gradually, the user can then fill in a target number field 44, representing the number of cigarettes per week by which the user wishes to cut back.

Figure 5:
FIG. 5 is an example screen mode for a graphical user interface for use in designating quit tactics in some embodiments of the present disclosure.
Figure 5:
Figure 5:

In a tactics screen mode, shown in FIG. 5, the user can select from a menu of daily options, or tactics, for reducing number of cigarettes smoked, by selecting a graphical box 50 corresponding to each tactic the user wishes to plan for.

In some embodiments, a first tactic is giving up the easiest cigarettes of the day, a second tactic is to only smoking during certain hours, and a third tactic is not smoking in certain situations, such as, for example, while driving. Alternatively, in some embodiments, if the user selects the third tactic, the graphical user interface can also present a write-in text field (not illustrated) for the user to write in descriptive text describing the situations in which the user wishes to remember as a non-smoking situations.

Figure 6:
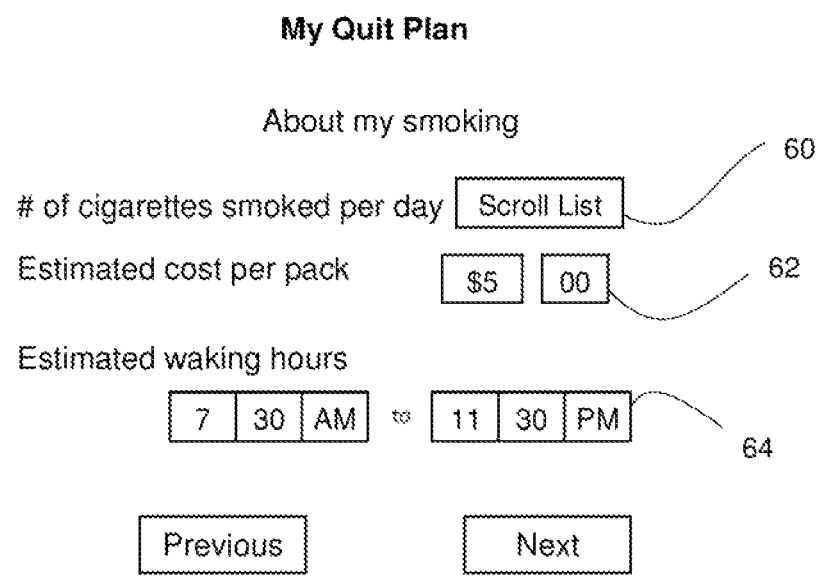
FIG. 6 is an example screen mode for a graphical user interface for use in inputting a user smoker's profile in some embodiments of the present disclosure.

As shown in FIG. 6, in a smoker's profile screen mode, or "about my smoking" screen mode, the user can enter inputs for number of cigarettes smoked per day in field 60, and cost per pack of cigarettes in field 62. Estimated waking hours for the user can be entered in field 64. The app can use the information entered in the smoker's profile screen mode to calculate an estimate of the cost per month for cigarettes. The cost can be presented in the quit plan summary screen mode (discussed below). This feedback can enhance the user's motivation to quit smoking. In some embodiments, the estimated waking hours can be used by the app to time daily push notifications, including, for example, (1) text invitations or other audio and/or display reminders to view one of the quit smoking exercises and (2) text invitations or other audio and/or display reminders to track progress in quitting for the day (tracking progress can include, for example, tracking urges passed, or the restraint from unwanted behavior despite the existence of an urge(s), or urge awareness, or tracking engagements in unwanted behavior, such as, for example, each time the user has smoked). For example, in various embodiments, one or more automated notifications may be displayed to the user to remind the user to select either a first indicia (which when selected by the user indicates that the user has tracked an acceptance of an urge to smoke regardless of whether the user acts on the urge by smoking) or a second indicia (which when selected by the user indicates that the user has tracked refraining from smoking by allowing the urge to pass and not smoking), each automated notification to be displayed only when a threshold period of time has passed since user's last selection of either the first indicia or the second indicia. In some embodiments, the timing of the notifications are determined by an algorithm, which can be, for example, a random time interval in the first three (3) hours of the user's waking hours, a random time interval between six (6) and nine (9) hours after the user is awake, and a random time interval of within three (3) hours of the user going to sleeping.

Alternatively, in other embodiments, the number of notifications received during a day can vary, and can be three (3), more than three, or less than three. Alternatively, in some embodiments, the notifications, or random notifications, can be generated at different times other than those expressly disclosed herein.

In some embodiments, a user is presented with a medication screen mode, such as that shown in FIG. 7, in which the user can select from a list of medications which user uses, or intends to use, to aid in quitting smoking. The user can designate the relevant medication by, for example, selecting a graphical box 70 corresponding to a particular medication. These medications include, for example, the nicotine patch, nicotine gum, Varenicline, Welbutrin, and other medication of the user's choosing. In some embodiments, the symbol, "?," appears beside each selection when touched on the screen, which can be touched to display text that briefly describes each medication, how to obtain them on one's own, and how to use them. In some embodiments, the user may also select the option of an "other" medication for medication not listed or the option of no medication.

In some embodiments of the present disclosure, a user can select within the app, a support group to support the user in the process of quitting smoking. A support group setup screen mode, displaying one or more name fields 80 and email address fields 82, as illustrated in FIG. 8, can be selected by the user, wherein the user can enter one or more names and corresponding email addresses for people (e.g., up to ten people) from whom the user wants support during the process of quitting smoking. In some embodiments, one name field and email address field is displayed at a time, and the user can select to additional names and email addresses using the support group setup screen, in which case, additional name fields 80 and email address fields 82 are presented for use by the user. The names and email addresses can be entered manually or can be selected from the contact directory on the phone. For example, when a name field 80 or email field 82 is selected, the graphical user interface can present a browse contacts indicia, and if the user selects the browse contacts indicia, the user interface can present a screen on which the user can browse and scroll through the user's stored contacts and select a contact to automatically fill the name field 80 and email field 82.

Figure 9:
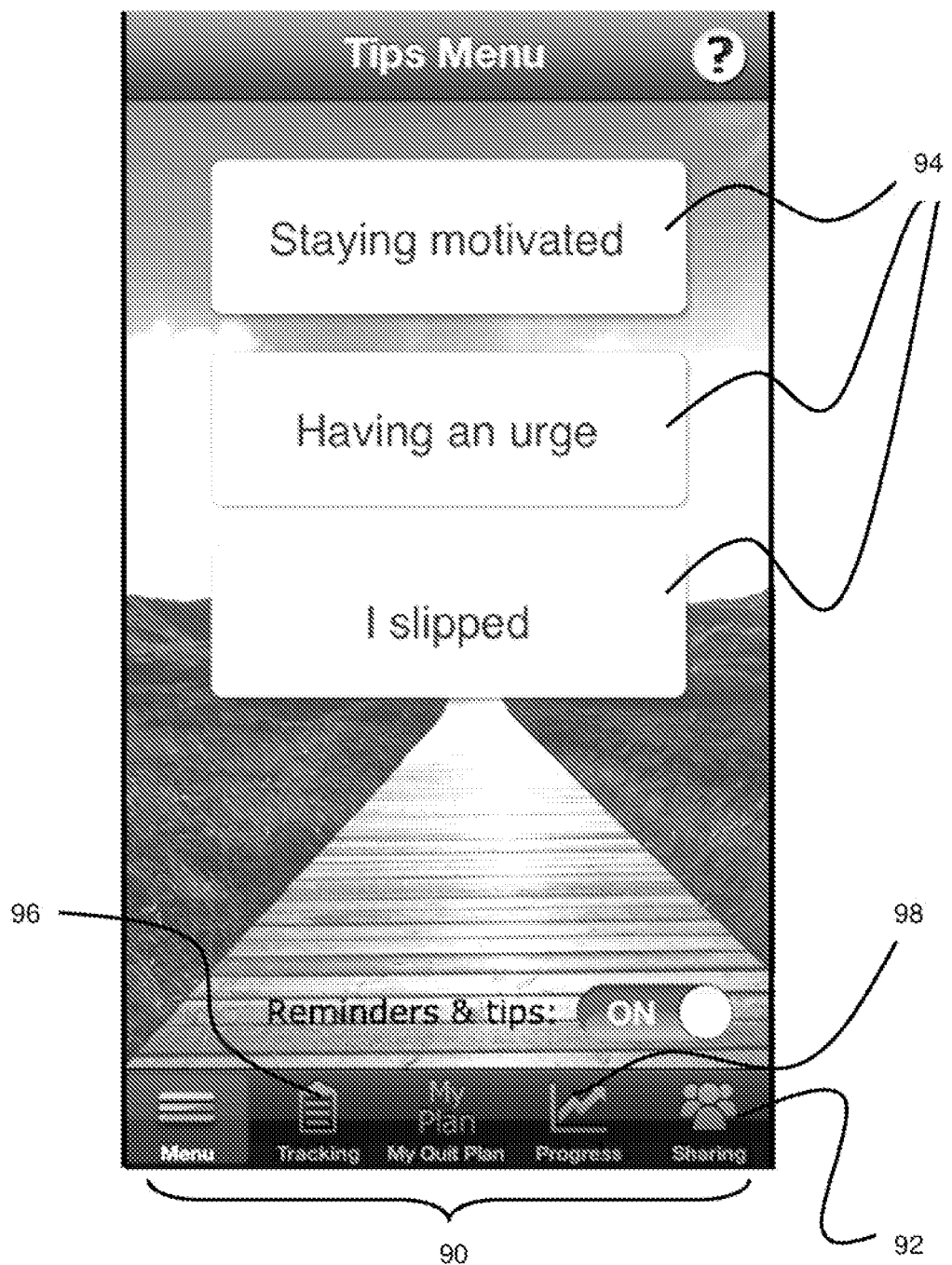
FIG. 9 is an example screen mode for a graphical user interface showing a tip menu and main menu in some embodiments of the present disclosure.

Referring to FIG. 9, a screen mode includes a tips menu having selectable tip type indicia 94 for viewing various associated submenus (as discussed further below), and a main menu 90 (as discussed further below), which can include, among other selections, a sharing indicia 92. The sharing indicia 92 can be labeled to indicate that the indicia is selectable for sharing when actuated by the user. If a user selects the sharing indicia 92, the graphical user interface can display a share screen mode (not illustrated), wherein a user can type in the user's progress, and the selected names and email addresses entered in the support group setup screen mode can be auto-populated, and the user can select to share the user's progress achieved.

Referring to FIG. 10, the information entered by a user in the screen modes for the quit plan setup (e.g., personal values screen mode, quit date screen mode, quit method screen mode, tactics screen mode, smoker's profile screen mode, medication screen mode, and support group setup screen mode), can be displayed in summary form on a quit plan summary screen mode. The quit plan summary screen mode, shown in FIG. 10, can include, for example, a listing of the user's selected life domains from the personal values screen mode (e.g., family, leisure, and "other," which can comprises a user-written life domain, as described, supra), the user's selected quit date from the quit date screen mode, the user's quit method from the quit method screen mode (e.g., cold turkey or a particular user selected number of cigarettes to cut back by per day or per week or per month, etc.), the user's selected quit tactics from the tactics screen mode (e.g., giving up the easiest cigarette of the day and only smoking during certain hours), the number of cigarettes the user smokes per day and the app calculated cost per month of that habit (from information provided by the user in the users smoker's profile screen mode), the medications the user intends to use from the medication screen mode, and the individuals the user wishes to rely on for support from the support group setup screen mode. The quit plan summary screen mode of FIG. 10 can be accessed by the user by selecting to view the quit plan summary screen mode from the main menu 90 (such as shown in FIG. 9). In some embodiments, the main menu 90 is accessible in most, if not all, screen modes of the graphical user interface.

Referring to FIG. 9, in some embodiments, the user can select from a plurality of tip type indicia 94, shown as a tip menu, and each tip type indicia 94 can represent a submenu. After a user has set up a quit plan, using the quit plan setup screen modes, the graphical user interface can display the tip menu screen mode of FIG. 9, along with the main menu 90, as an initial, or default screen mode, each time the user opens the app.

In some embodiments, there can be three (3) tip type indicia 94, and those tip type indicia can be labeled as "Staying Motivated," "Having an Urge," and "I Slipped," or can be labeled in terms having related or analogous meaning.

If a user selects the Staying Motivated indicia, a submenu associated with a plurality of ACT exercises can be displayed. In some embodiments, three selectable ACT exercises can be selected within this submenu, namely:

A) Selectable inspiring stories from which a user can select from a series of testimonials from former smokers describing how quitting smoking was motivated by core values:—for example, loving their spouse and children, caring for their bodies, and love of God. The testimonials can be presented in video with accompanying audio.

B) An exercise which can be designed to identify the smoker's deep motivations for quitting smoking. The exercise asks the user what the user would do in life if a magic wand made of all his problems disappear. The answers can serve as prompts for naming what is important to the person.

C) A graphical indicia labeled "Why I am Quitting" (or otherwise equivalently labeled) can be selected after which, the graphical user interface displays a randomly selected photo from the user's phone that symbolizes what is inspiring the user to quit smoking, and the randomly selected photo is an photo previously designated by the user during the quit plan setup screen modes, namely, the personal values screen mode.

If a user selects the tip type indicia 94 labeled "Having an Urge," the graphical user interface can present the user with eight selectable exercises comprising methods for assisting the user in allowing urges to pass. For example, a first exercise can be entitled, "Are you willing," and the exercise can involve the graphical user interface presenting text to the user instructing the user that every time the has urge, to try to allow it to pass on its own without smoking. The second exercise can be called "Tug of War," and the text can explain that dealing with urges is like having a tug of war with a monster—the urge monster, and that a solution to this problem is to drop the rope in the war with the urge monster. The third exercise can be called "Chinese Handcuffs," and that text can explain that urges are like being stuck in a tube of woven straw. The text can go on to explain that an intuitive way to escape is to try to pull out the fingers from the tube, which is like trying to avoid cravings; however, the counterintuitive way to escape is the method promoted by the app, which is to push in on the straw, equivalent to focusing one's attention on the urge, rather than trying to avoid it. The fourth exercise can be called "Stop and Breathe," and the text and associated video and audio can provide an exercise for the user to follow in breathing, when a craving to smoke occurs. The fifth exercise can be called "Leaves on a Stream," and the text and the video can ask the user to imagine a stream with leaves floating down it, wherein the leaves are thoughts that tempt the user to smoke. The goal of this exercise can be to let the thoughts about smoking float down the stream. The sixth exercise can be called "Carry Cards," and the text and accompany video/audio can ask the user to write down thoughts that trigger smoking a cards. The user is instructed to carry these cards with him throughout the day and then tap the cards with his hand when he has the particular thoughts written on the cards. The goal of this exercise can be to distance the user from the thoughts that trigger smoking. The seventh exercise can be called "I'm Having the Thought." and the text and the audio can ask the user to add the phrase "I'm having the thought . . . " to every thought he has that triggers him to smoke. The goal of this exercise can be to distance the user from the thoughts that trigger smoking. The eighth exercise can be called "Sky and Weather," and the text and the audio can ask the user to imagine their cravings to smoke as like clouds in the sky. The user can then be asked by the text and/or audio to notice that beyond the clouds is the endless sky. The goal of this exercise can be to help the user understand that there is an endless quality to their being that goes beyond cravings that they feel at any one moment in time.

The "Having an Urge" exercises above can teach a user to let an "urge pass" by allowing an urge to be there, or to accept it, or to be willing to have it, or to notice it, or to observe it, without acting out the unwanted behavior that is the subject of the urge. Also, regardless of whether the user acts out unwanted behavior, the "Having an Urge" exercises can teach a user to allow the urge to be there, or to accept it, or to be willing to have it, or to notice it, or to observe it (e.g., being aware of the urge).

In some embodiments, the user can select the tip type indicia 94 labeled "I Slipped," and in response, the app can present the user with a plurality of exercises that the user can select from that are methods for recovering from relapse. The first exercise can be called "Puppy exercise," and the text and the audio can ask the user to imagine a puppy almost being injured (e.g., almost hit by a car). This exercise can be designed to elicit feelings of compassion and caring toward the puppy. The exercise asks the user whether the user would give the puppy a cigarette to comfort it. Since the obvious answer is no, the next question the exercise asks the user whether is whether the user would give himself/herself a cigarette when upset? The goal of this exercise can be to take a self-compassionate perspective when the user is stressed, rather than to have a cigarette. The second exercise can be called "Letter from the future," and the text and the audio ask the user to write himself a letter ten years from the future, where he has gained a lot of experience and wisdom as a non-smoker. The exercise asks what advice this future self would give the present self about how to quit smoking. The third exercise can be called "Compassion for Yourself," and the text and the audio can ask the user to go gentle on himself when he is self-critical about the process of quitting smoking. Instead, the user is invited to learn from a relapse. The fourth exercise can be called "Getting Back on the Road," and the text and the audio can ask the user to imagine slipping, that is, having a cigarette. It asks the user to imagine that slipping is part of the journey of quitting smoking and encourages him to start again at any time in the process of quitting smoking. In alternative embodiments for each of the tip types discussed, additional exercises can be provided, or fewer exercises can be provided.

Figure 11:
FIG. 11 is an example screen mode for a graphical user interface for use in tracking activities or events in some embodiments of the present disclosure.

In some embodiments of the present disclosure, various tracking features are provided by the app. Referring to FIG. 9, a user can select the tracking indicia 96 from the main menu 90, to initiate a tracking screen mode. An example tracking screen mode is shown in FIG. 11, which can allow a user to track daily progress in quitting smoking. As shown in FIG. 11, the tracking screen mode can include data fields 112, 114, 116, 118 for the user to indicate number of times smoked 112, number of times the user has let smoking urges pass without acting on them 114, number of times the user has practiced tip exercises within the app 116, and number of times the users has used quit medications 118. The tracking screen mode in FIG. 11 can be configured to receive data representing a single day, so that the fields are used for entering data representing the current day, and can each field can automatically reset to zero (0) on the next day. In some embodiments, each field 112, 114, 116, 118 can have corresponding plus (+) and minus (−) selection indicia 110, proximate thereto, such that a user can select the plus indicia (e.g. by tapping or touching the indicia) to incrementally increase the number indicated in the corresponding field, and can select the minus indicia (e.g. by tapping or touching the indicia) to incrementally decrease the number indicated in the corresponding field. As will be appreciated by those skilled in the art immediately upon reviewing this disclosure, either plus (+) or minus (−) selection indicia 110 can be represented by other graphical representations, such as, graphical buttons of any of a variety of shapes or sizes.

In further example embodiments (not illustrated), alternative data fields for tracking (which can include selectable indicia, such as a graphical button for adjusting numerical selection, similar to the plus (+) and minus (−) indicia discussed, supra) can include not only tracking the number of times that the user allows urges to pass, but also the number of times the user consciously allows an urge to be there, or accepts it, or is willing to have it, or takes notice of it (is aware of it), or observes it. For example, such a data field could be labeled by indicia that conveys "accepted an urge," or "experienced an urge" or "aware of an urge and observed it," or some other equivalent indicia, such that the user could track both allowing an urge to pass, and/or acceptance of an urge, regardless of whether the user allowed it to pass without acting on it. Also, the user could be presented with exercises (e.g., the "Having an Urge" exercises) or display screen modes, that teach through text, audio, video or pictures, not only that allowing an urge to pass can mean, "allowing an urge to be there, accepting an urge, being willing to have an urge, taking notice of an urge, or observing an urge, and not acting on unwanted behavior that is the subject of the urge," but also that, accepting an urge can mean "allowing an urge to be there, accepting an urge, being willing to have an urge, taking notice of an urge (being aware of it), or observing an urge, regardless of whether the unwanted behavior that is the subject of the urge is acted on." As will be appreciated by those skilled in the art after reviewing this disclosure, various terms can be substitutes for these that are equivalent or similar in meaning.

Figure 12:
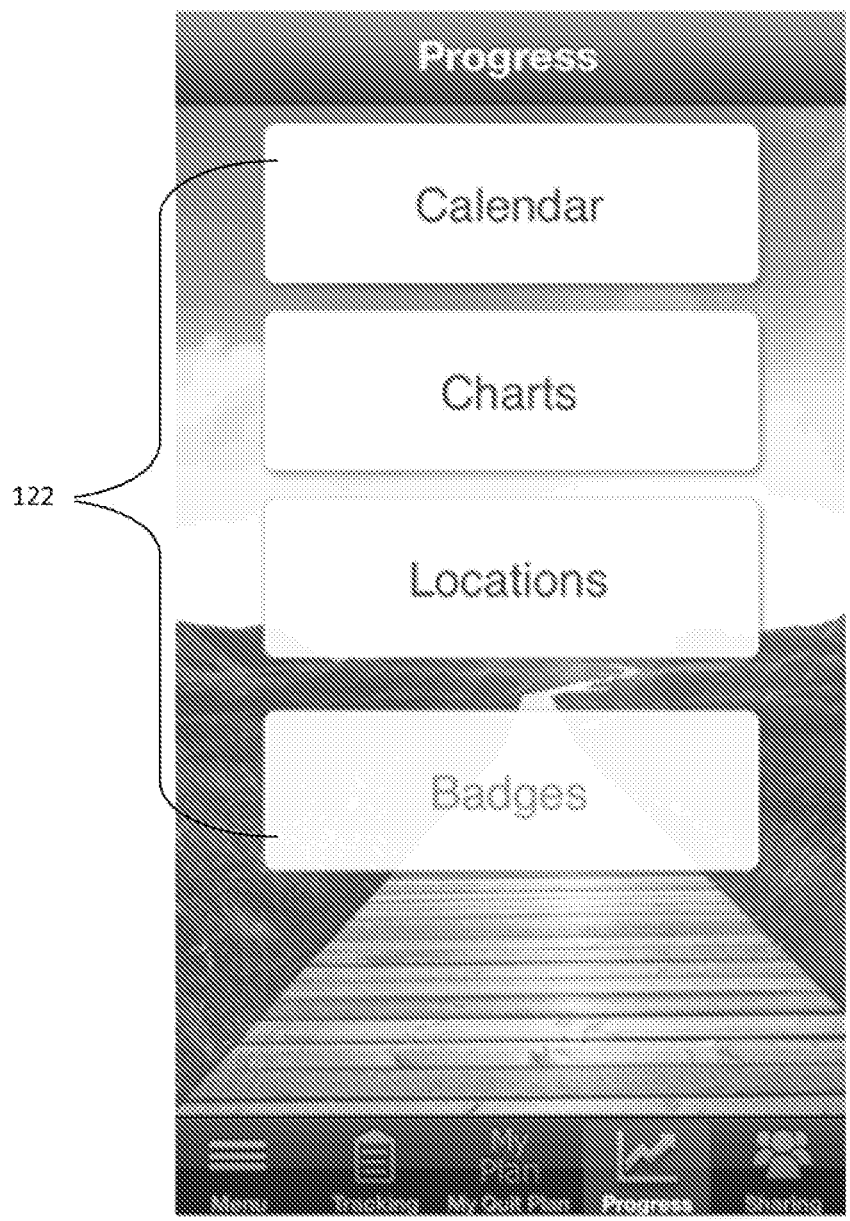
FIG. 12 is an example screen mode for a graphical user interface showing a menu of selectable indicia for selecting various ways to view progress or monitor activities or events in some embodiments of the present disclosure.

In some embodiments of the present disclosure, a user can select to view progress data, by selecting the progress indicia 98 from the main menu 90, as shown in FIG. 9. Upon user selection of the progress indicia 98, the graphical user interface can display a progress screen mode, as shown in FIG. 12. The progress screen mode can include a plurality of selectable monitoring indicia 122. The monitoring indicia 122 can comprise, for example, indicia for selecting to view calendars, charts, location data, and badges. In some embodiments, monitoring indicia 122 can be viewed without first accessing a progress screen mode, but may be selectable for other screen modes, or from any screen mode.

Figure 13:
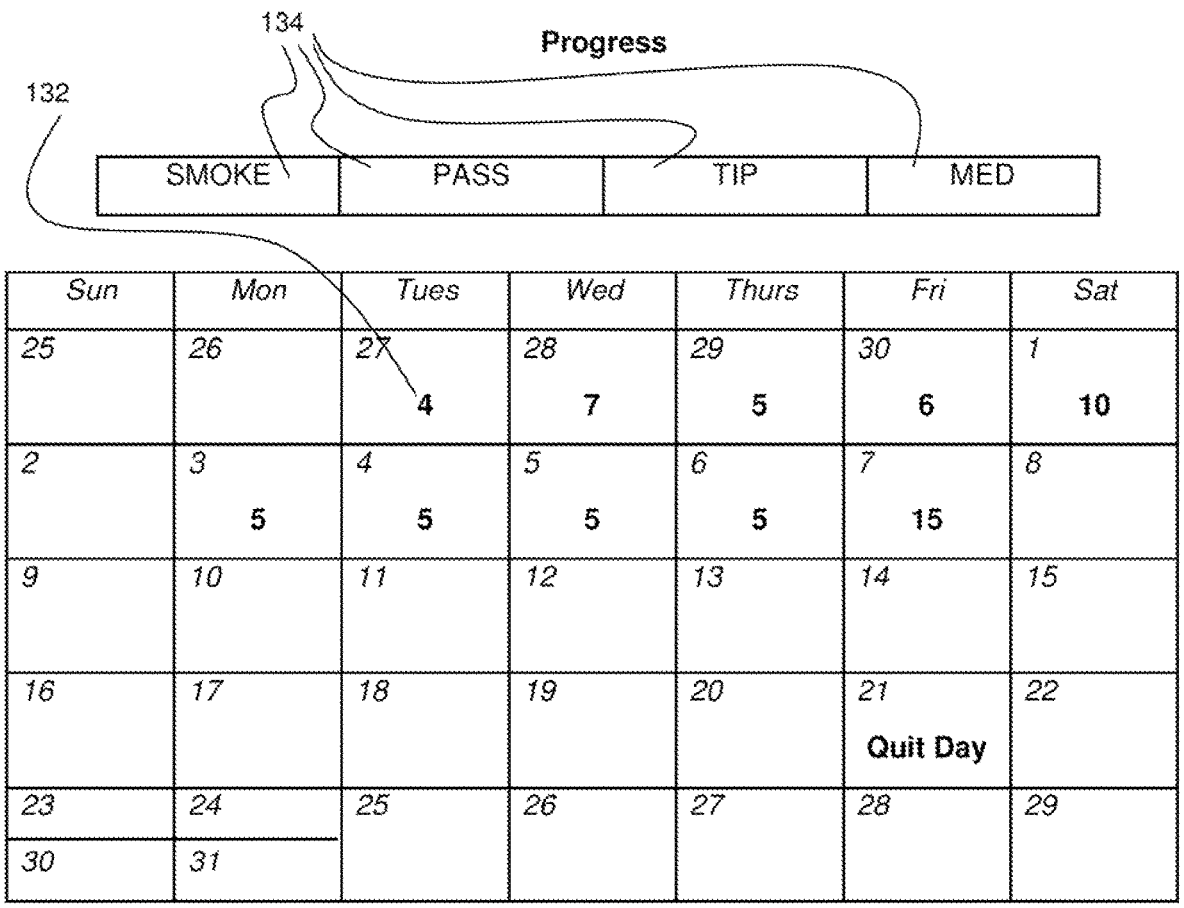
FIG. 13 is an example screen mode for a graphical user interface showing a calendar for viewing progress or monitoring activities or events in some embodiments of the present disclosure.

If the user selects indicia for viewing calendars, the graphical user interface can display a calendar screen mode, such as that shown in FIG. 13, wherein the calendar can display daily numerical indicia 132 representing a number of events having occurred on that particular day, the event represented by the number depending on the particular calendar type selected. For example, in some embodiments, the calendar screen mode in FIG. 13 can include selectable calendar type indicia 134, the calendar type indicia can be labeled, for example, SMOKE, PASS, TIP and MED. For example, if the user selects the calendar type indicia labeled "SMOKE," the numerical indicia 132 shown in the calendar proximate each date (e.g., within a graphical box containing the date) can represent the number of times a user smoked on that particular day, as recorded by the user in the tracking screen mode of FIG. 11. Likewise, if the user selects the calendar type indicia labeled "PASS," the numerical indicia 132 shown in the calendar proximate each date can represent the number of times a user let an urge pass on that particular day, as recorded by the user in the tracking screen mode of FIG. 11. If the user selects the calendar type indicia labeled "TIP," the numerical indicia 132 shown in the calendar proximate each date can represent the number of times a user practiced a tip exercise within the app on that particular day, as recorded by the user in the tracking screen mode of FIG. 11. If the user selects the calendar type indicia labeled "MED," the numerical indicia 132 shown in the calendar proximate each date can represent the number of times a user used medication on that particular day, as recorded by the user in the tracking screen mode of FIG. 11. As will be appreciated by those skilled in art immediately upon reviewing this disclosure, in some embodiments, similar, different, or additional, events can be tracked by number of occurrences and displayed in the calendar screen mode, in association with dates in which they occurred on a calendar display, such as, for example, those parameters recorded using alternative data fields for tracking discussed above (e.g., the number of times the user consciously allows an urge to be there, or accepts it, or is willing to have it, or takes notice of it, or observes it).

Figure 14:
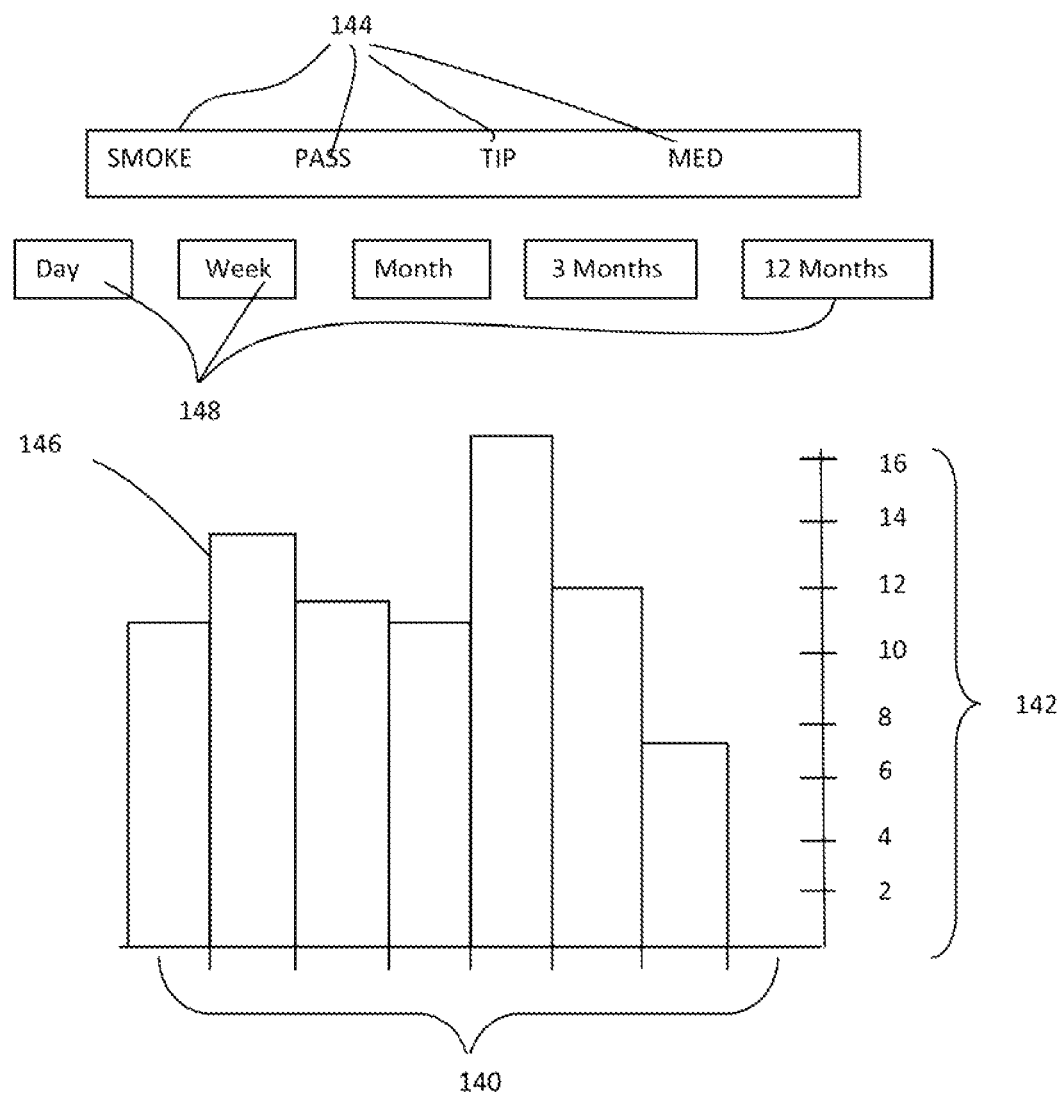
FIG. 14 is an example screen mode for a graphical user interface showing a chart for viewing progress or monitoring activities or events in some embodiments of the present disclosure.

If the user selects indicia for viewing charts, the graphical user interface can display a chart screen mode, such as that shown in FIG. 14, wherein the chart can display data in graphical form, representing a number of events having occurred over a particular period. For example, in some embodiments, the chart screen mode in FIG. 14 can include selectable chart type indicia 144, the chart type indicia can be labeled, for example, SMOKE, PASS, TIP and MED, or any other terms signifying data representing the numbers of times a user smoked, the number of times a user allowed an urge to smoke pass without smoking, the number of times the user practices one of the tip exercises (as described above), and the number of times the user used quit assistance medication. In addition, the chart screen mode of FIG. 14 can include selectable chart interval indicia 148, for use in selecting the time interval and/or time units reflected in the chart screen mode. For example, if the user selects the chart type indicia labeled "SMOKE," and the chart interval indicia 148 labeled "Week," then each of the graphical bars 146 can represent a day in a week, over a one week interval of time, while the height of each bar can be proportional to the number of cigarettes smoked by the user on the particular day of the week represented by the particular graphical bar 146, as will be appreciated by those skilled in the art after reviewing this disclosure. The vertical axis units can represent the number of events having occurred, the event being represented depending on the selected chart type indicia 144.

Figure 15:
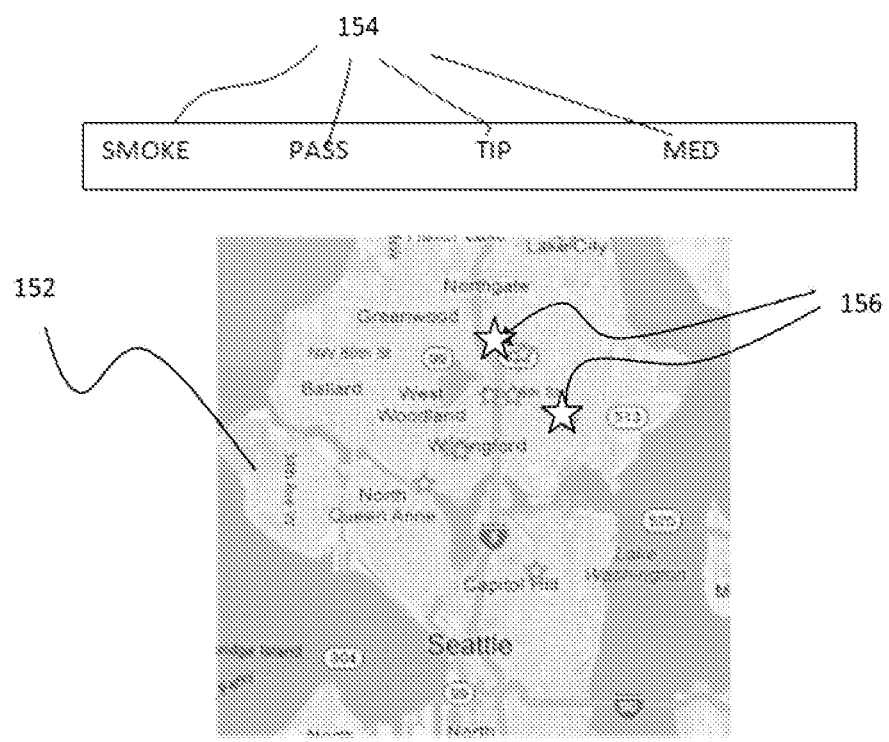
FIG. 15 is an example screen mode for a graphical user interface showing a map for viewing progress or monitoring activities or events in association with location information in some embodiments of the present disclosure.

In some embodiments of the present disclosure, if the user selects indicia for viewing locations from the monitoring indicia 122, a locations screen mode can be displayed, as illustrated generally in FIG. 15. In the locations screen mode, the user can select from various location date-type indicia 154. The location data-type indicia can be labeled, for example, SMOKE, PASS, TIP and MED, or any other terms signifying data representing, respectively, locations where the user has smoked, allowed an urge to smoke pass without smoking, practiced one or more tip exercises (as described above), or used quit assistance medication. For example, in some embodiments, when a user uses the tracking screen mode of FIG. 11 to track an event, such as by increasing the number(s) in any of the fields representing the number of times smoked 112, the number of times the user has let smoking urges pass without acting on them 114, the number of times the user has practiced tip exercises within the app 116, or the number of times the users has used quit medications 118, the app can access the user's smart device GPS (if permitted by a user), to record the location at which the user recorded an increase in the number. The app can record the location in association with the particular event, such as, for example, a particular number of cigarettes smoked, in connection with the location. Thus, the location data can thereafter be displayed by type, selectable using the location data-type indicia 154. That is, in some embodiments, when the user selects the particular data type representing a type of activity (e.g., where the user smoked, by selecting SMOKE), one or more location markings (e.g., marked by graphical stars in FIG. 15), can show where this even has occurred. In some embodiments, the graphical stars could be clustered in particular locations, which may tend to show that an event is occurring frequently in that location (e.g., smoking, practicing a tip, allowing an urge to pass, etc.). If the user is diligent about tracking the user's activity at, or near the time it occurs, then the location screen mode will tend to be more reflective of the user's progress or activities, as will be appreciated by those skilled in the art after reviewing this disclosure.

In some embodiments of the present disclosure, if the user selects indicia for viewing badges from the monitoring indicia 122, a badges screen mode can be displayed, which can display graphical representations of badges earned by the user for achieving milestones in the quitting process. The badges can be graphical indicia, or otherwise, graphical representations of badges awarded to the user by the app for completing activities (e.g., practicing tips, completing a quit plan, etc.), or avoiding smoking by letting urges pass and tracking those events in the tracking screen mode.

Figure 16:
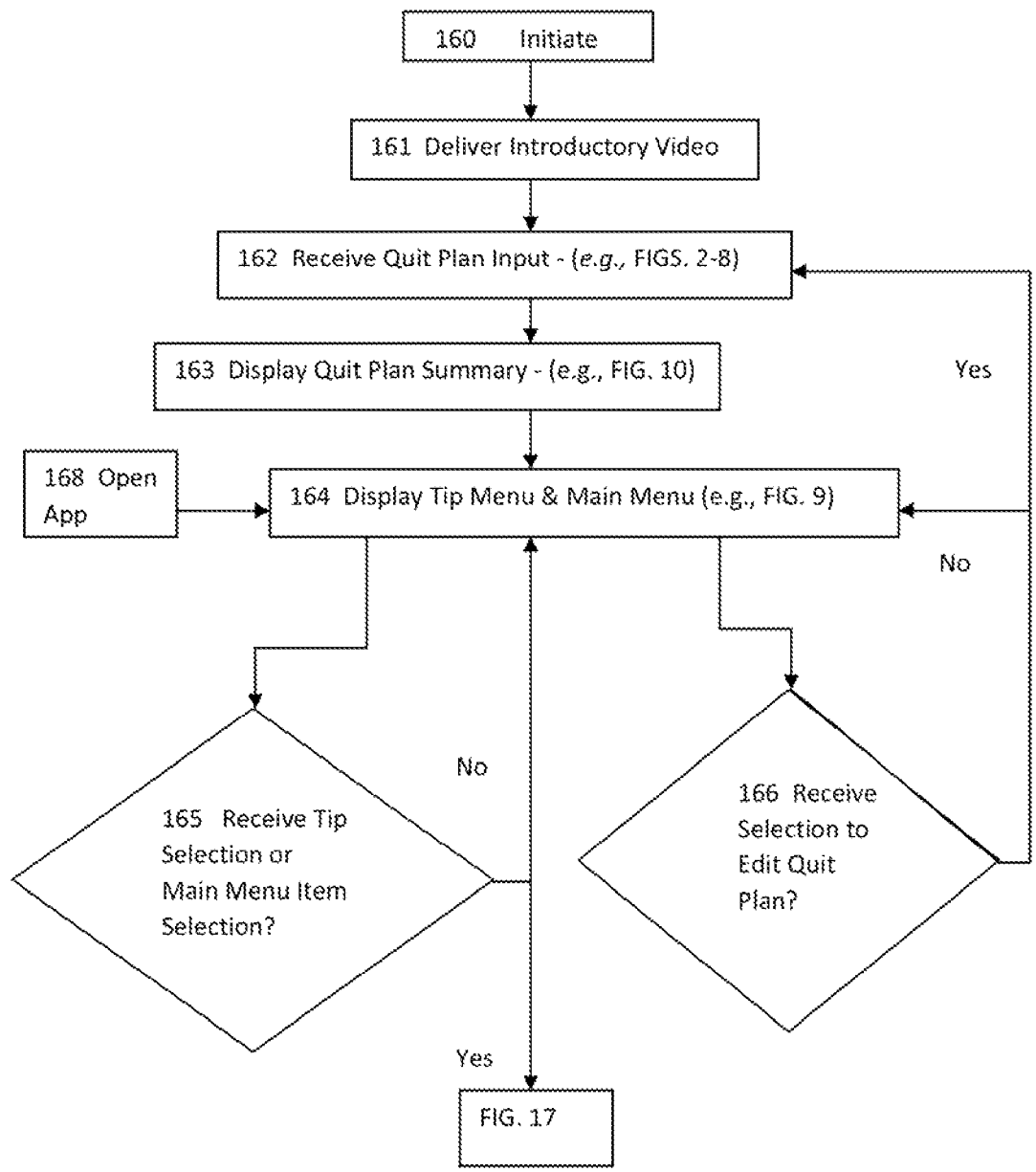
FIGS. 16-17 are simplified flow diagrams for some embodiments of the present disclosure for assisting a user in habit cessation.
Figure 17:
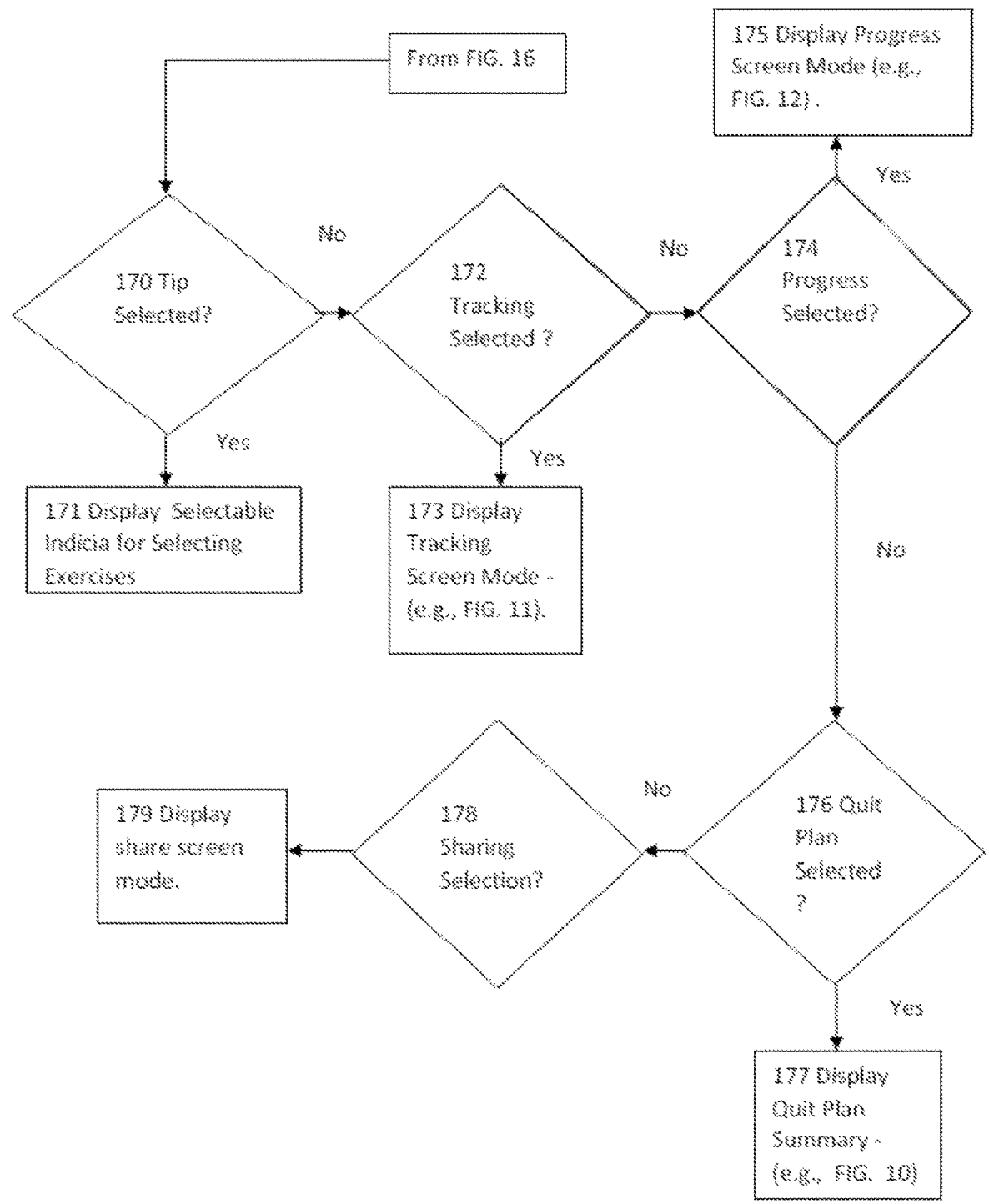

In addition, FIGS. 16 & 17 illustrate a working example overview flowchart for some of computer implemented methods disclosed here, which include the graphical user interface modes described above, and there relationship to one another and associated methods for use, but exclude the examples described above designated as "alternative" embodiments. In particular, for the working example, as shown in FIG. 16, when the app was first initiated at step 160, the introductory video (accompanied by audio) was presented to the user at step 161, as described, supra. The user was then presented with various screen modes (as described above in connection with FIGS. 2-8), in which the app collected input from the user at step 162 for use in setting up a quit plan. After data collection for setting up the quit plan was complete, the app caused display of a quit plan summary at step 163, namely, the quit plan summary illustrated in FIG. 10. The app then directed the user to a main menu and/or tip menu at step 164. Also, after a quit plan had been generated by collecting input from the user, thereafter, when the app was opened (e.g., step 168), the home screen mode was the main menu combined with the tip menu (shown in FIG. 9). At step 166, the user could select to edit the quit plan at any time from the main menu.

Continuing with the working example, referring to FIG. 17, at step 170, the user could select from the tip type indicia 94 (shown and described in relation to FIG. 9), upon which, the app caused the display of a submenu for selecting exercises at step 171. The exercises described/categorized, supra, for "Staying Motivated," "Having an Urge," and "I Slipped, are were all part of the working example. At step 172, the user could select tracking indicia from the main menu, upon which, the app could cause the tracking screen mode (shown and described in relation to FIG. 11) to be displayed at step 173, which the user could use to track progress. At step 174, the user could select a progress indicia 98 from the main menu, upon which, the app could cause the progress screen mode (shown and described in relation to FIG. 12) to be displayed at step 175. At step 176, the user could select to view a summary of the user's quit plan, upon which, the app caused the quit plan summary (shown and described in relation to FIG. 10) to be displayed at step 177. At step 178, the user could select the share indicia from the main menu, upon which, the app caused a share screen mode to be displayed in which the user can type a status update, and send to the user's selected support group, at step 179, as described, supra. Also, reminders or push notifications were sent as described above, including invitations to view one of the quit smoking exercises, track progress in quitting for the day.

In a confidential, double blind randomized trial of one hundred and ninety-six (196) participants, the working example computer implemented method disclosed above, was compared with the US Government's QuitGuide app for smoking cessation. On the primary outcome of 30-day point prevalence abstinence at two months post randomization, the disclosed working example had 62% to 88% descriptively higher rates of quitting using the standard missing=smoking imputation. Specifically, for all randomized participants (N=196), the quit rates were 13% for the working example disclosed herein vs. 8% in QuitGuide (OR=2.7; 95% CI=0.8-10.3). Among those at baseline smoking at least a pack a day (n=35), the quit rates were 11% in for the working example disclosed herein vs. 6% in QuitGuide (OR=1.8; 95% CI=0.1-53.3). The 13% vs. 8% quit rates for the main outcome suggests that for every 500,000 smokers (recall there are 42 million smokers in the US alone), an additional 25,000 adults would quit smoking by using the working example disclosed herein, as compared to using QuitGuide. Consistent with ACT's theory of change, among those at baseline scoring low (below the median) on acceptance of cravings (n=88), the quit rates were 15% for the working example disclosed herein vs. 8% in QuitGuide (OR=2.9; 95% CI=0.6-20.7). Utilization predicted cessation: those who opened the working example app at least 16 times (following the recommendation of twice a week for eight weeks) had six times higher odds of quitting smoking as compared to those opening it less than 16 times (OR=5.9; 95% CI=1.1-30.5). While the pilot design did not make it possible to conduct formal mediational analysis, from baseline to the two-month follow-up, there was an increase in acceptance of cravings in the working example arm (p<0.04) but not in the QuitGuide arm (p=0.15)—again consistent with ACT's theory of change. High acceptance of cravings (i.e., scoring above the median) was strongly associated with 30-day point prevalence abstinence at 2-month follow-up (OR=6.1; 95% CI=3.0-15.2).

Features used by participants during the trial that were most predictive of the 30-day point prevalence abstinence at 2 months post randomization were (1) tracking practice of acceptance skills (Odds Ratio (OR)=16.4; p=0.01) (e.g., tracking acceptance of an urge), (2) viewing one's quit plan (OR=11.1; p=0.03), (3) practicing letting urges pass (OR=10.5; p=0.03), (4) viewing a specific "Staying Motivated" testimonial (OR=4.1; p=0.06), and (5) viewing a specific "Having an Urge" acceptance exercise (OR=4.1; p=0.06). Odds ratios of 4.1 to 16.4 mean that using the feature was predictive of four to sixteen times higher odds of quitting.

In some alternative embodiments of the present disclosure, the app can generate push notifications, or other notifications within the graphical user interface, as a function of input provided by the user, and experimental data. For example, input provided by the user during the setup of the user's quit plan at step 162 in FIG. 16, can be used to identify similarly situated experimental trial participants, and data related to the similarly situated trial participants can be used to generate push notifications. For example, users who indicate in their tracking that they are smoking more than 20 cigarettes in a given day (pack a day or more), may be sent a push notification stating that: "People who smoke at least a pack a day had 83% higher quit rates with the [working example] than a leading national app for quitting smoking."

In some alternative embodiments, when users fail to perform certain exercise (e.g., tracking urge acceptance, including number of times the user is aware of an urge, or number of times a user lets an urge pass) that have been shown in past research to have generated higher quit rates, the app can automatically send the user push notifications, or other notifications, that recite data from past research and recite a statistical link based on that research to the certain exercises. For example, the notification can include text stating that, "People practice letting their urges pass are ten times more likely to quit smoking. Tracking your urges now!" In some alternative embodiments, such notifications can be triggered when users have not practiced the exercises, or activities, such as, for example, urge exercises, or tracking activities, for a threshold period of time. The app can detect that the threshold period has passed based on the user's data entry (e.g. data entry in the tracking screen mode). In other alternative embodiments, the app can automatically track whether the user has completed certain exercises to monitor the user's exercise frequency and to determine whether a threshold period has passed. The threshold period of time could be, for example, three (3) days. In other embodiments, the threshold could be longer than three days, or shorter than three days.

As described previously in relation to the locations screen mode, illustrated generally in FIG. 15, the app can be used to track locations at which the user smokes. In some alternative embodiments, the app can send notifications to the user when the user is in a location in which the user has demonstrated past tendencies to smoke. Furthermore, in some alternative embodiments of the present disclosure, the app can drive the user's smart device 2 to record not only (1) the location of smoking using GPS, but also (2) the sound of the voices of the people near the user using the microphone. Recording could be manually triggered by the user directly, or by the user tracking an event in the tracking screen mode. The recording could also be triggered in response to the app sensing a location in which the user has smoked before, or by signal from a sensor (as described further below).

The sound of a voice recorded may be identified using widely available voice recognition technology, and stored on the user's smart device by the app, and then later matched if the voice is detected again. Thus, the app can later present the user with data indicating the frequency with which certain people smoke with the user, so that the user can be aware of a potential link between particular individuals and the user's tendency to smoke. Also, the app can automatically send notifications to the user when certain voices are detected if those voices are associated by the app with smoking activities of the user (e.g., a particular recorded voice is associated with two or more instances of smoking). The notifications sent as a results of voice recognition could be any of the types of notifications noted in this disclosure, including, for example, reminders to a user to practice all or certain exercises, or to track events or activities it the tracking screen mode.

Also, referring to FIG. 1, in some alternative embodiments, an external input device 22 attached to the user's smartphone, can be a carbon monoxide sensor (not specifically illustrated). The app can interface with, or contain, software for receiving signals from the carbon monoxide sensor to detect when the user is likely smoking. If smoking is detected, the app can automatically, through the user's smartphone, cause a notification to be sent (e.g., push notification) to the user, inviting the user to practice an exercise within the app. Also, when app detects that the user is likely smoking, the app can record a location of the user through a GPS of the user's smartphone, or smart device. Also, along with, or separate from recording the location of the user, the app can drive a microphone system of the user's smartphone to record voices in the proximity of the user, with such recording being triggered by the app detecting that the user is smoking through the carbon monoxide sensor. As described above, a voice recognition system on the user's smart device can then compare it against prior recorded voices to determine if the voice matches prior recorded voices.

After reviewing the present disclosure, an individual of ordinary skill in the art will immediately appreciate that some details and features can be added, removed and/or changed without deviating from the spirit of the invention. Reference throughout this specification to "one embodiment," "an embodiment," "additional embodiment(s)" or "some embodiments," means that a particular feature, structure or characteristic described in connection with the embodiment(s) is included in at least one or some embodiment(s), but not necessarily all embodiments, such that the references do not necessarily refer to the same embodiment (s). Furthermore, the particular features, structures, or characteristics may be combined in any suitable manner in one or more embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for assisting in smoking cessation comprising:
    displaying, by a smart device, one or more screen modes to receive a target date for a user to quit smoking;
    displaying, by the smart device, a screen node displaying a first indicia and a second indicia;
    receiving, by the smart device, an input in response to the user tapping the first indicia that indicates that the user has tracked an acceptance of an urge to smoke regardless of whether the user acts on the urge by smoking;

receiving, by the smart device, an input in response to the user actuating the second indicia that indicates that the user has tracked refraining from smoking by allowing the urge to pass and not smoking;

displaying, by the smart device, one or more automated notifications to remind the user to select either the first indicia or second indicia, each automated notification to be displayed when a threshold period of time has passed since user's last selection of either the first indicia or the second indicia;

recording audibly, by the smart device, one or more voices of one or more persons near the smart device when a global positioning system (GPS) of the smart device detects that the user is in a location in which the user has engaged in smoking;

storing, by the smart device, the recording of the one or more voices for matching if the one or more voices are detected again; and displaying, by the smart device, progress information to a user in relation to the smoking cessation, including displaying a number of times the user has tracked acceptance of the urge, regardless of whether the user acted on the urge, and displaying a number of times the user has refrained from smoking by allowing the urge to pass and no smoking.

2. The method of claim 1 wherein the first indicia for tapping multiple times, each tap after the initial tap of the first indicia to indicate that the user has tracked an addition acceptance of an additional urge to smoke regardless of whether the user acts on the additional urge by smoking, and wherein the second indicia for actuating multiple times, each actuation after the initial actuation of the second indicia to indicate that the user has tracked an additional refraining from smoking from an additional urge by allowing the additional urge to pass and not smoking.

3. The method of claim 1 further comprising:

displaying one or more auto-triggered reminders, reminding the user to track a) a number of exercises the user has completed related to acceptance of urges or b) the number of times the user has accepted the urge regardless of whether the user engaged in the unwanted behavior, where the auto-triggered reminders are displayed when a threshold period of time has passed based on the user's last data entry.

4. The method of claim 1 further comprising:

receiving a user selection to engage in an exercise, and in response to the selection, conveying through audio, text, pictures or video, one or more testimonials from individuals that previously engaged in unwanted behavior that is the subject of the user's behavior adjustment.

5. The method of claim 1 further comprising:

receiving a user selection to engage in an exercise, and in response to the selection, conveying through audio, text, pictures or video, reasons why the user is adjusting behavior as a function of information the user previously provided in response to queries in a screen mode.

6. The method of claim 5 wherein the information provided by the user comprises photos previously selected by the user.

7. The method of claim 1 further comprising:

receiving a user selection to engage in an exercise, and in response to the selection, conveying through audio, text, pictures or video, methods or techniques for accepting urges or allowing urges to pass.

8. The method of claim 1 further comprising, receiving a selection from the user to track the user's engagement in one or more exercises, and displaying indicia to the user indicating a number of times the user has engaged in the one or more exercises.

9. The method of claim 1 wherein tapping the first indicia increases or decreases a displayed numerical value.

10. The method of claim 9 further comprising receiving a user selection of a screen mode displaying a calendar showing a number of acceptance of urges the user has tracked in association with corresponding dates on which the acceptance of urges were tracked.

11. The method of claim 1 further comprising displaying a screen mode showing one or more graphically represented badges, each of the badges being indicative of one or more tracked activities having been completed.

12. The smart device of claim 11 wherein instead of displaying a screen mode having the first indicia and second indicia, the first indicia and second indicia are substituted with hardware buttons that form an exterior surface of the smart device, wherein the buttons can be actuated to provide the inputs corresponding to the inputs otherwise provided by the first indicia and second indicia.

13. A method for assisting in smoking cessation using a portable smart device, the method comprising:

displaying, by the smart device, through a screen mode at least a first selectable indicia associated with a visual or audio communication to a user inviting the user to track an urge to smoke when a user is aware of the urge receiving, by the smart device, data from the user provided by tapping of the first selectable indicia, the data including data indicative of the user having experienced the urge and smoked;

displaying, by the smart device, through the screen mode at least a second selectable indicia in association with a visual or audio communication inviting the user to track when the user has allowed the urge to pass without smoking;

receiving, by the smart device, data from the user provided by selection of the second selectable indicia, the data being indicative of the user having refrained from smoking after experiencing the urge;

displaying, by the smart device, a progress screen or calendar screen showing data as a function of a number of times the user has selected the first selectable indicia or the second selectable indicia within specific time periods;

displaying, by the smart device, one or more automated notifications to remind the user to select either the first selectable indicia or second selectable indicia, each automated notification to be displayed when a threshold period of time has passed since user's last selection of either the first selectable indicia or the second selectable indicia;

recording audibly, by the smart device, one or more voices of one or more persons near the portable smart device when a global positioning system (GPS) of the smart device detects that the user is in a location in which the user has engaged in smoking;

storing, by the smart device, the recording of the one or more voices for matching if the one or more voices are detected again;

displaying, by the smart device, one or more user interface screens for a user to enter data describing the user's motivations for quitting smoking, including a list of inquiries to which the user responds using fields for data entry;

receiving, by the smart device, data from the user regarding the user's motivations for quitting smoking; and displaying, by the smart device, a third selectable indicia for selecting to display the data regarding the user's motivations for quitting.

14. The method of claim 13 further comprising displaying a quit plan comprising a description of the user's motivations for quitting smoking, and a target quit date.

15. The method of claim 14 wherein displaying the quit plan further comprises displaying a quit method or quit tactic.

16. The method of claim 13 further comprising displaying a current financial cost of smoking for the user.

17. The method of claim 13 further comprising automatically notifying the user to practice an exercise when a location tracking system detects that the user is near a location in which the user has smoked according to a tracking function.

18. The method of claim 13 further comprising receiving a user selection to engage in an exercise, and in response to the selection, conveying through audio, text, pictures or video a) a request that asks the user what the user would do in life if all the user's problems disappear, b) a story of an animal that is almost injured, c) a request to the user to imagine that the user has adjusted behavior in the future and should consider what advice the user would give to the user from that future position, d) an instruction to the user to have self-compassion, or e) an explanation to the user that engaging in the unwanted behavior while the user is trying to adjust behavior is a part of a journey.

19. A computer implemented method of assisting in smoking cessation using a portable smart device comprising:

displaying, by the portable smart device, a screen mode inviting a user to track urges to smoke without regard to whether a user smokes, including a first indicia that is tapped by a user to indicate an acceptance of an urge regardless of whether the user acts on the urge by smoking and a second indicia that can be tapped to indicate that the user has tracked reframing from smoking despite having an urge to smoke;

displaying, by the portable smart device, a plan of the user that describes the user's tactics for behavior adjustment;

displaying automatically, by the portable smart device, one or more notifications to remind the user to track the urges to smoke when a threshold time period has passed after occurrence of user's last urge tracking data entry was entered;

recording audibly, by the portable smart device, one or more voices of one or more persons near the smart device when a global positioning system (GPS) of the smart device detects that the user is in a location in which the user has engaged in smoking; and storing, by the portable smart device, the recording of the one or more voices for matching if the one or more voices are detected again.

20. The computer implemented method of claim 19 further comprising displaying one or more screen modes for use in tracking or monitoring a number of exercises the user has completed.

\* \* \* \* \*